(12) United States Patent
Sullivan

(10) Patent No.: US 10,940,324 B2
(45) Date of Patent: Mar. 9, 2021

(54) WEARABLE CARDIOVERTER DEFIBRILLATOR (WCD) SYSTEM COMPUTING HEART RATE FROM NOISY ECG SIGNAL

(71) Applicant: West Affum Holdings Corp., Grand Cayman (KY)

(72) Inventor: Joseph L. Sullivan, Kirkland, WA (US)

(73) Assignee: West Affum Holdings Corp., Grand Cayman (KY)

( * ) Notice: Subject to any disclaimer, the term of this patent is extended or adjusted under 35 U.S.C. 154(b) by 128 days.

(21) Appl. No.: 15/948,884

(22) Filed: Apr. 9, 2018

(65) Prior Publication Data

US 2018/0318593 A1    Nov. 8, 2018

Related U.S. Application Data

(63) Continuation-in-part of application No. 15/880,853, filed on Jan. 26, 2018, now abandoned.
(Continued)

(51) Int. Cl.
*A61B 1/00* (2006.01)
*A61N 1/39* (2006.01)
(Continued)

(52) U.S. Cl.
CPC .......... *A61N 1/3987* (2013.01); *A61B 5/0002* (2013.01); *A61B 5/0245* (2013.01);
(Continued)

(58) Field of Classification Search
USPC .......................................................... 607/5
See application file for complete search history.

(56) References Cited

U.S. PATENT DOCUMENTS 3,724,355 A    4/1973  Unger
4,583,524 A    4/1986  Hutchins
(Continued)

FOREIGN PATENT DOCUMENTS

WO    1998039061 A2    9/1998
WO    2016077786 A1    5/2016

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
(Continued)

*Primary Examiner* — Nicole F Lavert
(74) *Attorney, Agent, or Firm* — Spectrum IP Law Group LLC

(57) ABSTRACT

In embodiments, a WCD system includes electrodes with which it senses an ECG signal of the patient. A processor may detect sequential peaks within the ECG signal, measure durations of time intervals between the peaks, including between non-sequential peaks, and identify a representative duration that best meets a plausibility criterion. The plausibility criterion may be that the representative duration is the one that occurs the most often, i.e. is the mode. Then a heart rate can be computed from a duration indicated by the representative duration and, if the heart rate meets a shock condition, the WCD system may deliver a shock to the patient. An advantage can be that the representative duration can be close to a good R-R interval measurement of a patient, notwithstanding noise in the ECG signal that is in the shape of peaks.

14 Claims, 11 Drawing Sheets

SAMPLE COMPONENTS OF WEARABLE
CARDIOVERTER DEFIBRILLATOR (WCD)
SYSTEM

Related U.S. Application Data

(60) Provisional application No. 62/501,009, filed on May 3, 2017.

(51) Int. Cl.

| | | |
|---|---|---|
| *A61B 5/0245* | (2006.01) | |
| *A61B 5/00* | (2006.01) | |
| *A61B 5/024* | (2006.01) | |
| *A61B 5/046* | (2006.01) | |
| *A61B 5/0456* | (2006.01) | |
| *A61B 5/0408* | (2006.01) | |
| *A61B 5/044* | (2006.01) | |
| *A61N 1/02* | (2006.01) | |
| *A61N 1/08* | (2006.01) | |
| *A61N 1/04* | (2006.01) | |
| *A61B 5/08* | (2006.01) | |
| *A61B 5/1455* | (2006.01) | |
| *A61B 5/11* | (2006.01) | |
| *A61B 5/145* | (2006.01) | |
| *A61B 5/02* | (2006.01) | |
| *A61B 5/021* | (2006.01) | |
| *A61B 5/026* | (2006.01) | |
| *A61B 5/04* | (2006.01) | |
| *A61B 5/0468* | (2006.01) | |

(52) U.S. Cl.
CPC .......... *A61B 5/02438* (2013.01); *A61B 5/044* (2013.01); *A61B 5/046* (2013.01); *A61B 5/0408* (2013.01); *A61B 5/0456* (2013.01); *A61B 5/6823* (2013.01); *A61B 5/7203* (2013.01); *A61N 1/025* (2013.01); *A61N 1/3904* (2017.08); *A61B 5/0006* (2013.01); *A61B 5/021* (2013.01); *A61B 5/02028* (2013.01); *A61B 5/0261* (2013.01); *A61B 5/02405* (2013.01); *A61B 5/04011* (2013.01); *A61B 5/0468* (2013.01); *A61B 5/0816* (2013.01); *A61B 5/1112* (2013.01); *A61B 5/14542* (2013.01); *A61B 5/14551* (2013.01); *A61B 5/7275* (2013.01); *A61N 1/0484* (2013.01); *A61N 1/3968* (2013.01); *A61N 2001/083* (2013.01)

(56) References Cited

U.S. PATENT DOCUMENTS

| | | | |
|---|---|---|---|
| 4,619,265 A | 10/1986 | Morgan et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,427,083 B1 | 7/2002 | Owen et al. | |
| 6,437,083 B1 | 8/2002 | Brack et al. | |
| 6,529,875 B1 | 3/2003 | Nakajima | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 10/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,592,403 B2 | 3/2017 | Sullivan | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0070957 A1 | 3/2014 | Longinotti-Buitoni et al. | |
| 2014/0107541 A1* | 4/2014 | Sullivan ............... | A61N 1/3925 601/41 |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0328472 A1 | 11/2015 | Sullivan et al. | |
| 2016/0004831 A1 | 1/2016 | Carlson et al. | |
| 2016/0082277 A1 | 3/2016 | Foshee, Jr. et al. | |
| 2016/0220832 A1 | 8/2016 | Sullivan et al. | |
| 2016/0243374 A1 | 8/2016 | Sullivan et al. | |
| 2017/0136251 A1 | 5/2017 | Sullivan | |

OTHER PUBLICATIONS

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

(56) References Cited

OTHER PUBLICATIONS

Heartstart MRx and XL AED Algorithm—Application Note, Jul. 2001, Edition 2 Philips Healthcare, USA.
The LifeVest Network/Patient Data Management System, Zoll, 2015, 2000503 Rev A.
EP Search report for EPO Application No. 18 170 581.5, filed May 3, 2018.
Sooyeon Suh, Stress, Anxiety, and Heart Rate Variability in Chronic Obstructive Pulmonary Disease, Dissertation, 2010, The Ohio State University, Ohio USA.
Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

HEART RATE DETECTION FROM IDEALIZED, NOISE-FREE ECG SIGNAL FROM SINGLE CHANNEL

ESTABLISHING ALL POSSIBLE PEAK PAIRS

SAMPLE DURATIONS MEASURED IN NUMBERS OF SAMPLES

SAMPLE TIME DURATIONS, WITH CLUSTERS DISCERNED

SAMPLE DATA,
WITH CLUSTERS DISCERNED,
AND FURTHER
ACCOUNTING FOR FRACTIONS OF
HARMONICS

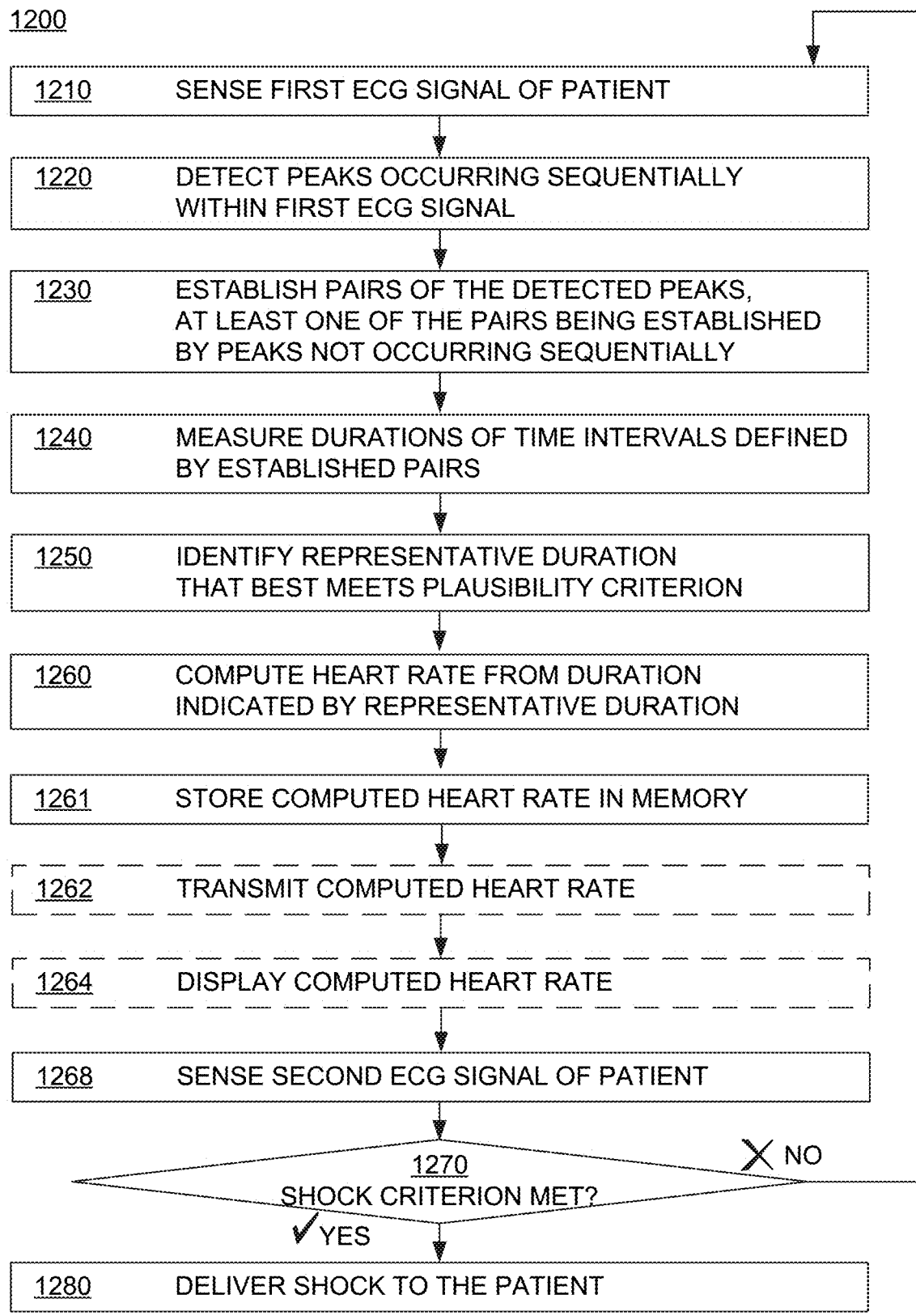
FIG. 12  METHODS

WEARABLE CARDIOVERTER DEFIBRILLATOR (WCD) SYSTEM COMPUTING HEART RATE FROM NOISY ECG SIGNAL

CROSS REFERENCE TO RELATED PATENT APPLICATIONS

This patent application is a continuation-in-part of U.S. application Ser. No. 15/880,853 filed on Jan. 26, 2018 (abandoned), and further claims the benefit of U.S. Application No. 62/501,009, filed on May 3, 2017.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

After being identified as having an increased risk of an SCA, and before receiving an ICD, these people are sometimes given a Wearable Cardioverter Defibrillator (WCD) system. (Early versions of such systems were called wearable cardiac defibrillator systems.) A WCD system typically includes a harness, vest, or other garment that the patient is to wear. The WCD system further includes electronic components, such as a defibrillator and electrodes, coupled to the harness, vest, or other garment. When the patient wears the WCD system, the external electrodes may then make good electrical contact with the patient's skin, and therefore can help sense the patient's ECG. If a shockable heart arrhythmia is detected, then the defibrillator delivers the appropriate electric shock through the patient's body, and thus through the heart.

A challenge in the prior art is that the patient's ECG signal may be corrupted by electrical noise. As such, it can be hard to interpret the ECG signal.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor. This approach in and of itself may also be inventive.

BRIEF SUMMARY

The present description gives instances of wearable cardioverter defibrillator (WCD) systems, storage media that store programs, and methods, the use of which may help overcome problems and limitations of the prior art.

In embodiments, a WCD system includes electrodes with which it senses an ECG signal of the patient. A processor may detect sequential peaks within the ECG signal, measure durations of time intervals between the peaks, including between non-sequential peaks, and identify a representative duration that best meets a plausibility criterion. The plausibility criterion may be that the representative duration is the one that occurs the most often, i.e. is the mode. Then a heart rate can be computed from a duration indicated by the representative duration and, if the heart rate meets a shock condition, the WCD system may deliver a shock to the patient.

An advantage can be that the representative duration can be close to a good R-R interval measurement of a patient, notwithstanding noise in the ECG signal that is in the shape of peaks.

These and other features and advantages of the claimed invention will become more readily apparent in view of the embodiments described and illustrated in this specification, namely from this written specification and the associated drawings.

BRIEF DESCRIPTION OF THE DRAWINGS

FIG. 12 is a flowchart for illustrating methods according to embodiments.

DETAILED DESCRIPTION

As has been mentioned, the present description is about wearable cardioverter defibrillator (WCD) systems, and related storage media, programs and methods. Embodiments are now described in more detail.

A wearable cardioverter defibrillator (WCD) system made according to embodiments has a number of components. These components can be provided separately as modules that can be interconnected, or can be combined with other components, etc.

Figure 1:
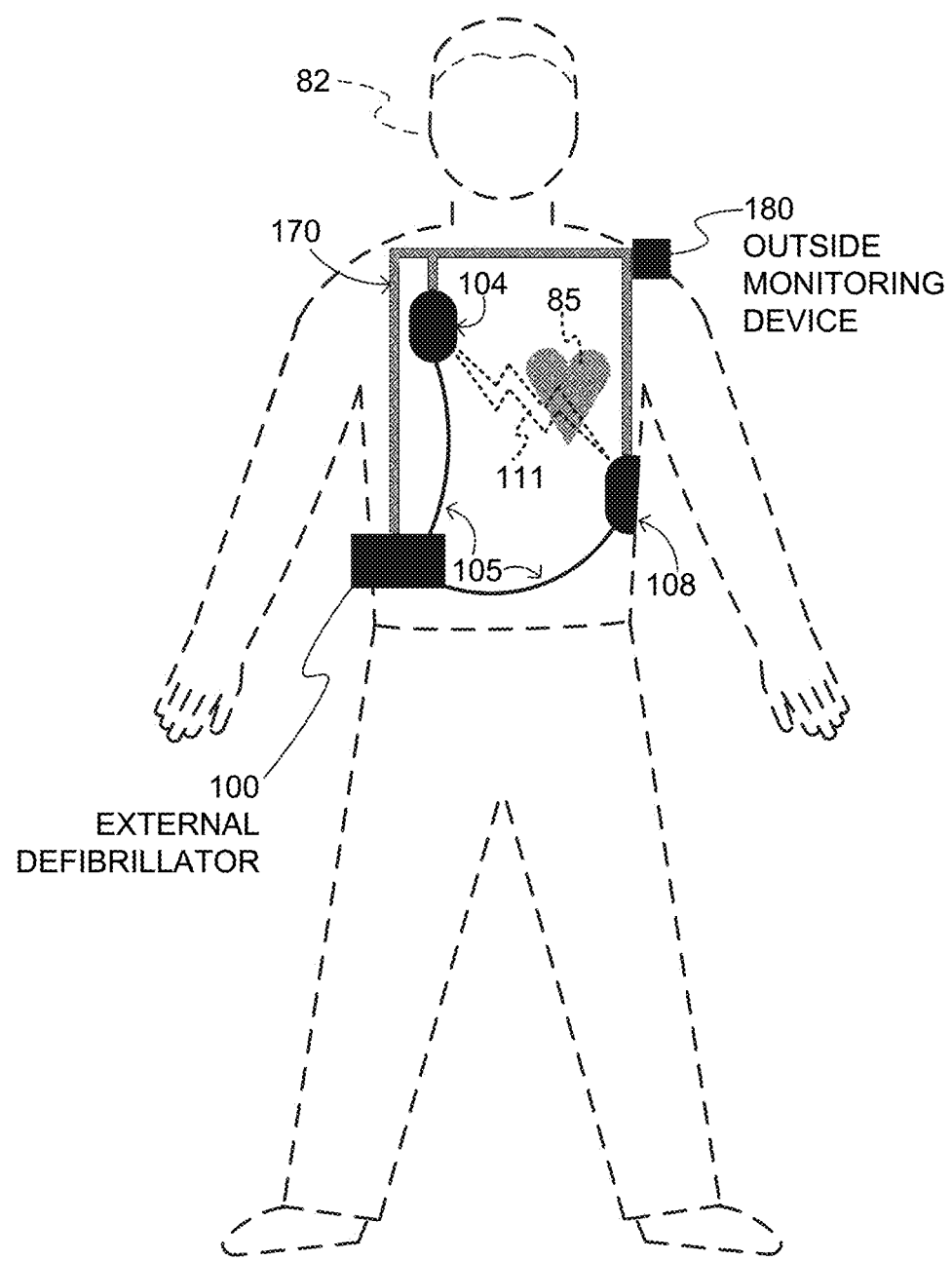
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means patient 82 can walk around, and is not necessarily bed-ridden.

FIG. 1 also depicts components of a WCD system made according to embodiments. One such component is a support structure 170 that is wearable by patient 82. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to parallel articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy and therapy shock. Pulse 111 is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, external defibrillator 100 may initiate defibrillation (or hold-off defibrillation) based on a variety of inputs, with ECG merely being one of them.

Accordingly, it will be appreciated that signals such as physiological signals containing physiological data can be obtained from patient 82. While the patient may be considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs or signals from one or more patient parameters that they sense.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
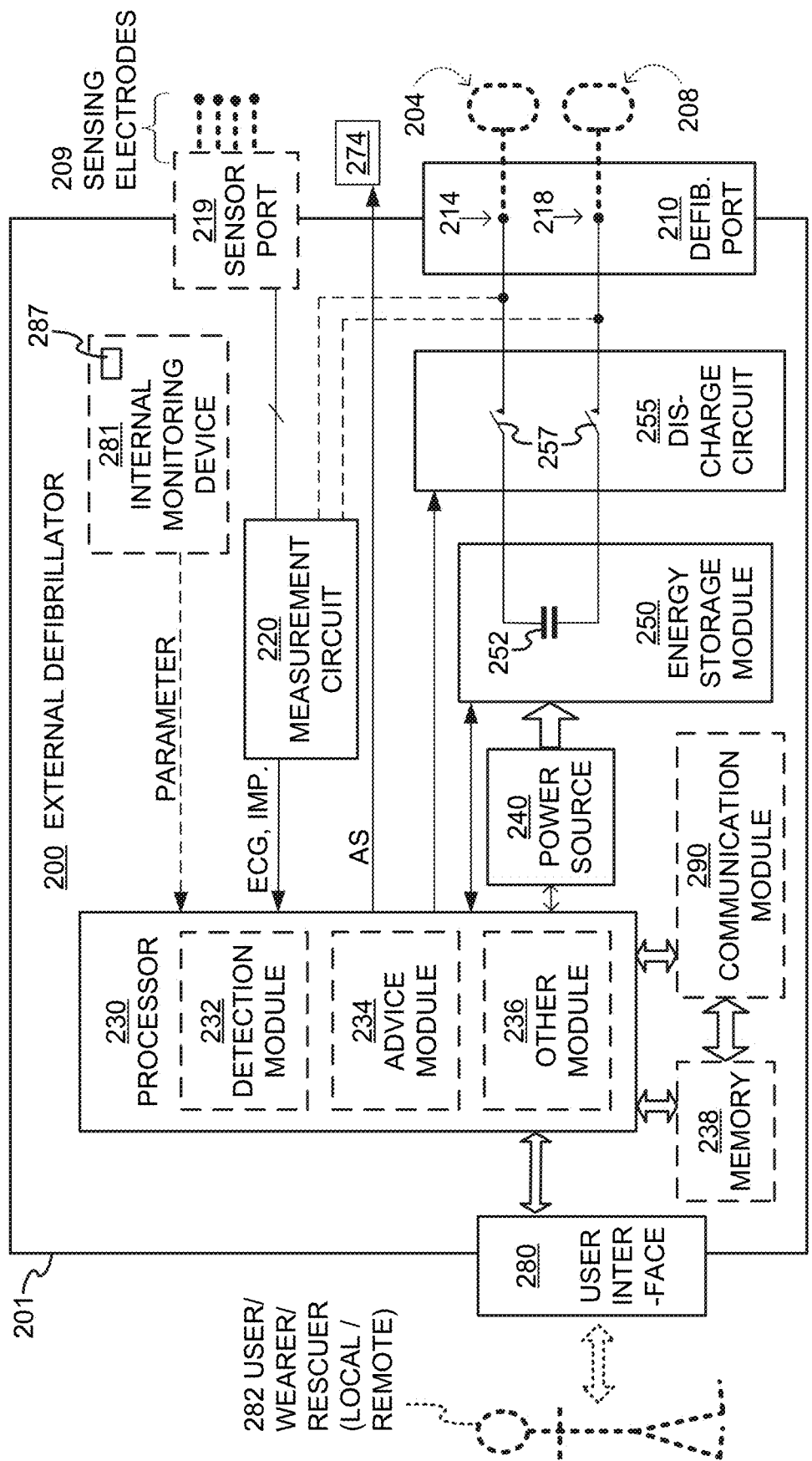
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281.

A motion detector of a WCD system according to embodiments can be configured to detect a motion event. In response, the motion detector may render or generate, from the detected motion event or motion, a motion detection input that can be received by a subsequent device or functionality. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. Sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away from the electrode, after it has been deployed. The fluid can be used for both defibrillation electrodes 204, 208, and for sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal AS from a processor 230, which is described more fully later in this document.

Figure 3A:
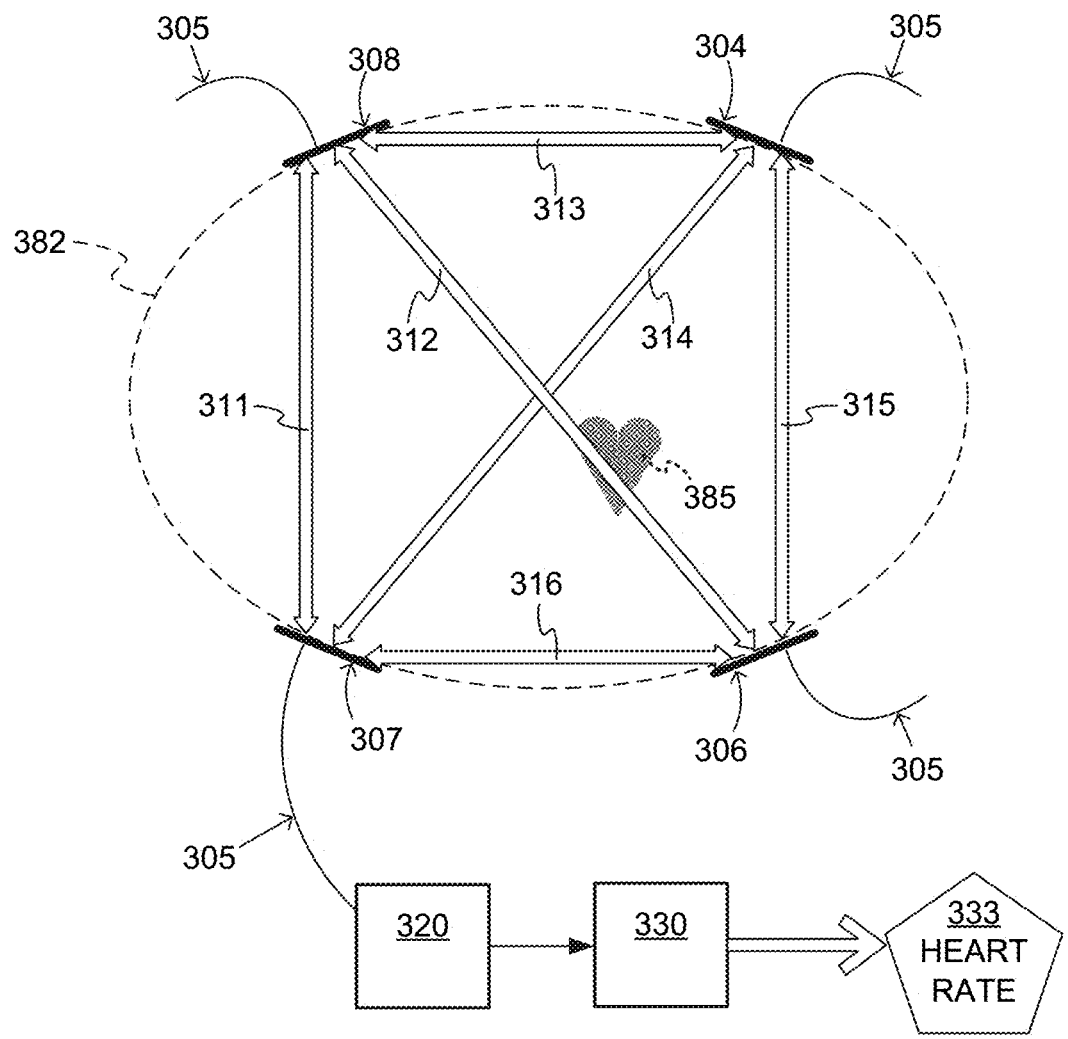
FIG. 3A is a conceptual diagram for illustrating how different electrodes may sense ECG signals of the patient along different vectors according to embodiments.

FIG. 3A is a conceptual diagram for illustrating how electrodes of a WCD system may sense or capture ECG signals along different vectors according to embodiments. A section of a patient 382 having a heart 385 is shown. There are four electrodes 304, 306, 307, 308, attached to the torso of patient 382, each with a wire lead 305. Any pair of these electrodes defines a vector, across which an ECG signal may be measured. These vectors are also known as channels and ECG channels. The four electrodes 304, 306, 307, 308 therefore can define six vectors, across which six respective ECG signals 311, 312, 313, 314, 315, 316 can be sensed. FIG. 3A thus illustrates a multi-vector situation. In FIG. 3A it will be understood that electrodes 304, 306, 307, 308 are drawn on the same plane for simplicity, while that is not necessarily the case. Accordingly, the vectors of ECG signals 311-316 are not necessarily on the same plane, either.

Any one of ECG signals 311-316 might provide sufficient data for making a shock/no shock determination. The effort is to shock when needed, and not shock when not needed. The problem is that, at any given point in time, some of these ECG signals may include noise, while others not. The noise may be due to patient movement or how well the electrodes contact the skin. The noise problem for a WCD may be further exacerbated by the desire to use dry, non-adhesive monitoring electrodes. Dry, non-adhesive electrodes are thought to be more comfortable for the patient to wear in the long term, but may produce more noise than a conventional ECG monitoring electrode that includes adhesive to hold the electrode in place and an electrolyte gel to reduce the impedance of the electrode-skin interface.

FIG. 3A also shows a measurement circuit 320 and a processor 330, which can be made as described for measurement circuit 220 and processor 230 later in this document. Processor 330 may further compute a heart rate 333 according to embodiments, as described in more detail further in this document.

Returning to FIG. 2, defibrillator 200 also includes a measurement circuit 220, as one or more of its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the physiological input reflects an ECG measurement. The patient parameter can be an ECG, which can be sensed as a voltage difference between electrodes 204, 208. In addition the patient parameter can be an impedance, which can be sensed between electrodes 204, 208 and/or the connections of sensor port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are sensed or captured according to embodiments, and determining whether a shock criterion is met. The determination can be made from a rhythm analysis of the sensed or captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. The data can include patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc. This way, data, commands, etc. can be communicated.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

Detection of the heart rate from the ECG signal is now described in more detail.

Figure 3B:
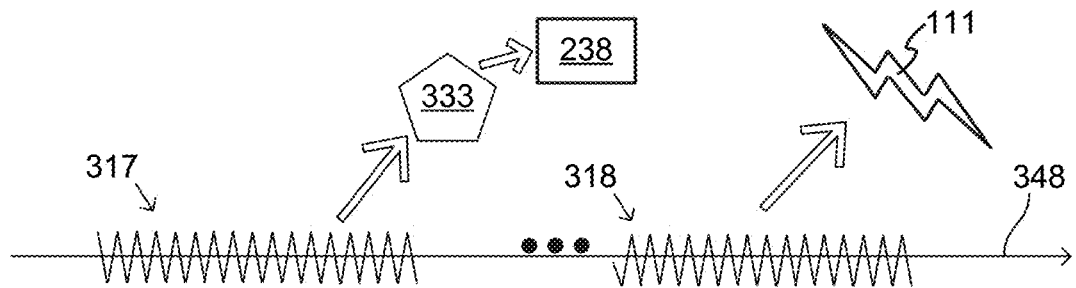
FIG. 3B is a conceptual diagram for illustrating how a first ECG signal may be used for in a heart rate computation while a second sensed ECG signal of the patient may be used for a shock decision according to embodiments.

FIG. 3B is a conceptual diagram that includes a time axis 348. A first sample ECG signal 317 and a second sample ECG signal 318 of the patient are shown with reference to time axis 348. Second ECG signal 318 has been sensed after sensing first ECG signal 317. It will be recognized that sample ECG signals 317, 318 indicate VT, but that is only for example. Either one of ECG signals 317, 318 may be sensed from any of the ECG channels or vectors of FIG. 3A, regardless of the fact that they are shown against the same time axis 348.

First ECG signal 317 may result in computing heart rate 333 according to embodiments. The computed heart rate 333 may be stored in memory 238, which is repeated in FIG. 3B. Heart rate 333 stored in memory 238 may then be downloaded later, transmitted wirelessly via communication module 290, displayed by a screen of user interface 280, and so on.

Second ECG signal 318 may be used to determine whether or not a shock criterion is met, for example by advice module 234. Second ECG signal 318 may or may not have been used to compute the heart rate according to embodiments.

If so, processor 230 may control, responsive to the shock criterion being met, discharge circuit 255 to discharge through patient 82 an electrical charge that is stored in energy storage module 250, while support structure 170 is worn by patient 82 so as to deliver a shock 111 to patient 82.

Figure 4:
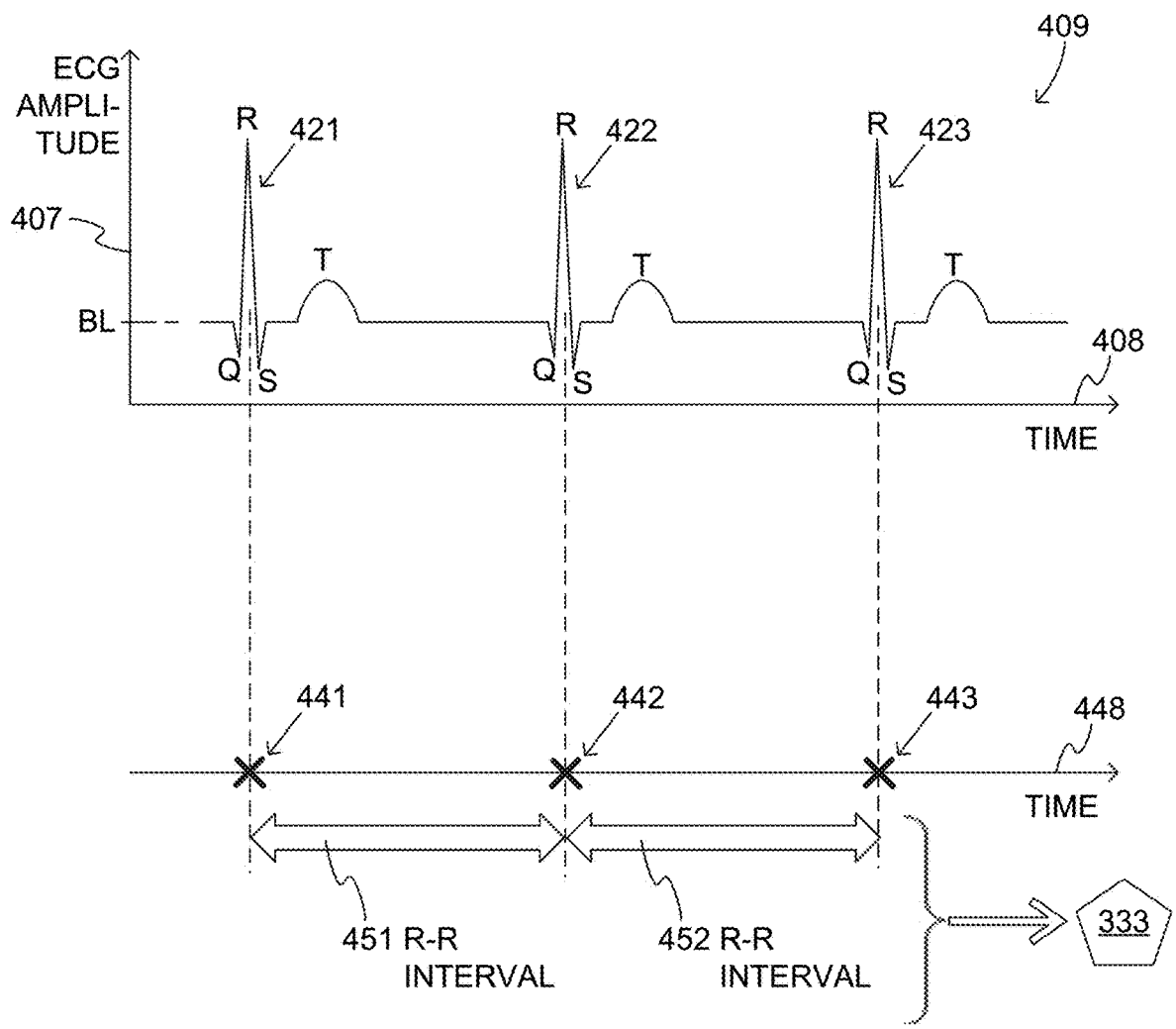
FIG. 4 shows time diagrams for illustrating how a patient's heart rate may be detected from a noise-free ECG signal in the prior art.

FIG. 4 shows an ECG signal in a time diagram 409. Diagram 409 has an ECG amplitude axis 407 and a time axis 408. Diagram 409 depicts a somewhat-idealized, noise-free ECG signal of patient 82, as it might be sensed from a single channel 311. The ECG signal of diagram 409 hovers around a horizontal baseline value BL. Baseline value BL can be considered to be zero, or it might be changing value due to noise, as described later in this document.

The ECG signal of diagram 409 includes three full heartbeats. In particular, three peaks 421, 422, 423 are shown, which occur sequentially. It will be recognized that peaks 421, 422, 423 are due to QRS complexes, each of which is followed by a T-wave of lesser amplitude. In this somewhat-idealized signal, a P-wave before the QRS complex and a U-wave after the QRS complex are not shown at all. The ECG signal of diagram 409 is further idealized in that the QRS complexes are shown as peaks, or spikes; in fact some heart rhythms have QRS complexes that don't look like spikes.

Peaks 421, 422, 423 are typically used for detecting the heart rate, because their large amplitude relative to the remainder of the ECG signal makes them more easy to identify and/or detect. In particular, FIG. 4 also shows another time axis 448. Time axis 448 indicates only the time occurrences 441, 442, 443 of peaks 421, 422, 423, respectively. Moreover, the successive peaks are considered in pairs to define time intervals. In particular, the pair of peaks 421 and 422 defines a time interval 451 from time occurrences 441, 442, while the pair of peaks 422 and 423 defines a time interval 452 from time occurrences 442, 443. Time intervals 451, 452 are sometimes called R-R intervals of the ECG signal. The durations of time intervals 451, 452 are measured, and heart rate 333 of the patient is thus computed from them.

It will be recognized that this process of computing heart rate 333 from peaks 421, 422, 423 in the ECG signal is the same regardless of how these peaks 421, 422, 423 are detected. Medical devices sometimes measure the ECG signal electronically and focus on these peaks to detect the R-R interval, for example as per the above. Other times, peaks 421, 422, 423 correspond with peaks in the patient's blood pressure, which can be sensed by someone placing their hand against the neck or a wrist of a patient.

It is more difficult, however, to measure the patient's heart rate from these peaks in the presence of noise in the ECG signal. An example is now described.

Figure 5:
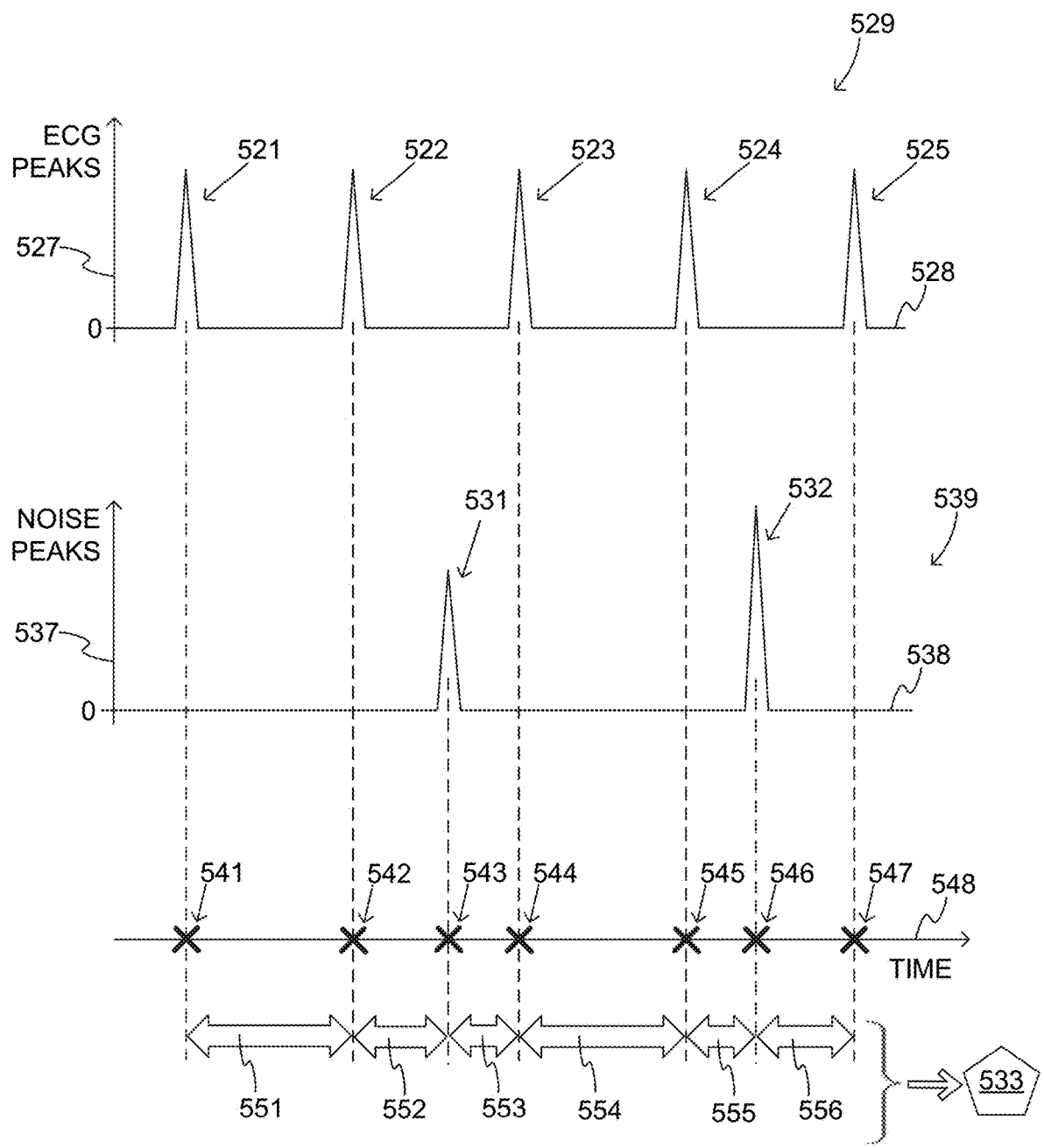
FIG. 5 is a time diagram for showing how noise in an ECG signal can corrupt the measurements used for the heart rate detection of FIG. 4.

FIG. 5 shows an ECG signal in a time diagram 529. Diagram 529 has an ECG peaks axis 527 and a time axis 528. Diagram 529 depicts only peaks 521, 522, 523, 524, 525 of an ECG signal, with all other values of the ECG signal being shown as zero for simplification. This simplification is acceptable in this instance, as FIG. 5 is used for discussing only the detection of the heart rate, and only by the peaks of the ECG signal.

FIG. 5 also shows a time diagram 539 to depict sample noise that could be added to the ECG of diagram 529. Diagram 539 has a Noise peaks axis 537 and a time axis 538. Diagram 539 depicts only peaks 531, 532 of noise, with all other values of the sample noise being shown as zero for simplification. In addition, noise peaks 531, 532 may have unequal amplitudes.

FIG. 5 further shows another time axis 548. Time axis 548 indicates only the time occurrences 541, 542, 543, 544, 545, 546, 547 of peaks 521-525 and also of peaks 531, 532. Time intervals 551, 552, 553, 554, 555, 556 can be used to compute a heart rate 533. It is clear, however, that these time intervals 551-556 are no longer true R-R intervals, as they were in the idealized noise-free case of FIG. 4, because of the noise in the ECG signal. As such, computed heart rate 533 may not be the true heart rate 333. Rather, in the situation of FIG. 5, the patient may be misdiagnosed with tachycardia due to noise peaks 531, 532.

In embodiments, however, the true heart rate 333 is measured, even in the presence of noise. Examples are now described.

Figure 6:
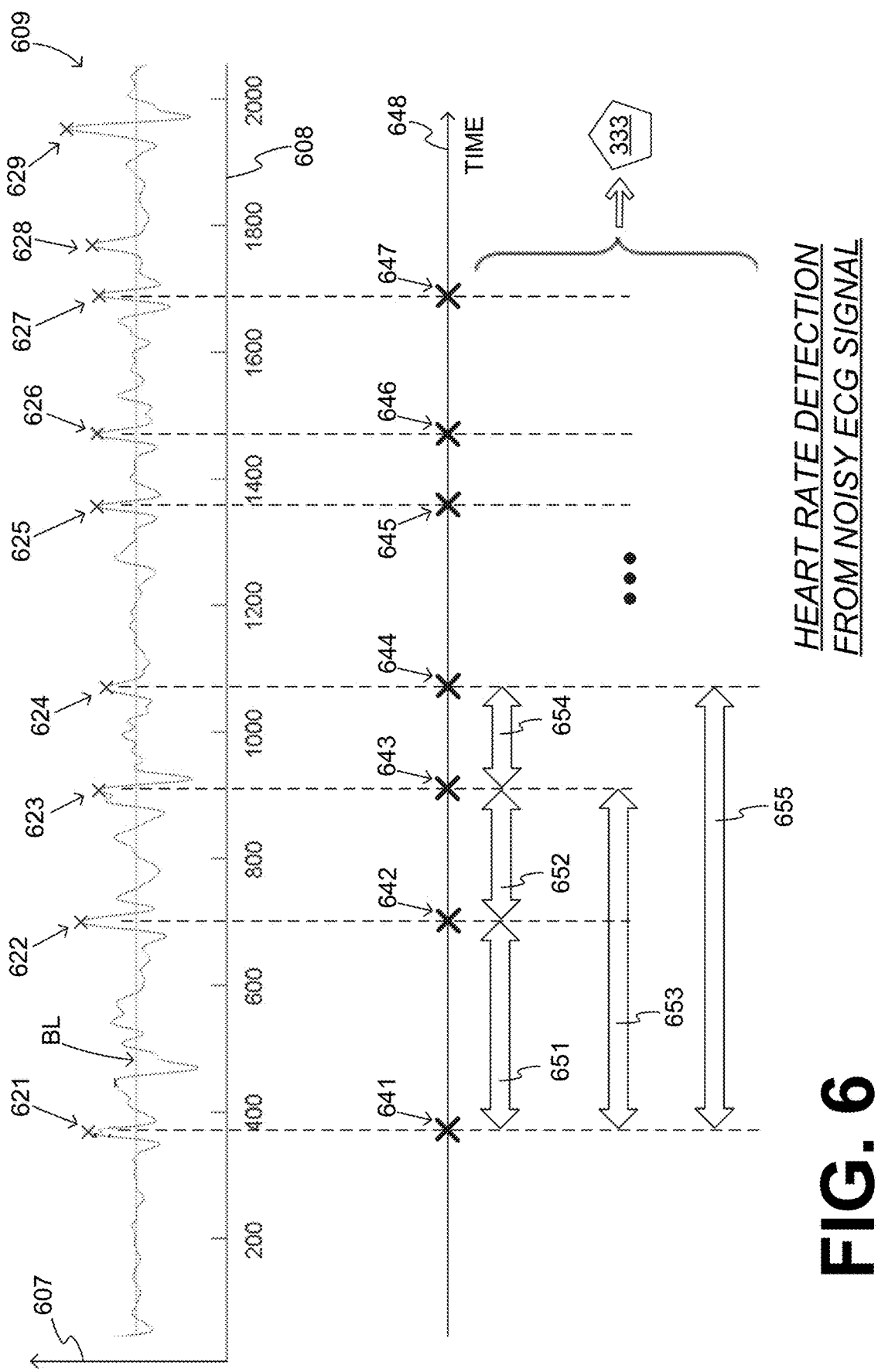
FIG. 6 is a time diagram for showing how a patient's heart rate may be detected from a noisy ECG signal according to embodiments.

Referring now to FIG. 6, a time diagram 609 has an ECG amplitude axis 607 and a time axis 608. Diagram 609 depicts an actual ECG signal of a patient. This ECG signal hovers around a horizontal baseline value BL. The units of time axis shows the ordinal number of a sample, i.e. $200^{th}$, $400^{th}$, etc.

In embodiments, peaks are detected, which occur sequentially within a sensed ECG signal. In the example of FIG. 6, peaks 621, 622, 623, 624, 625, 626, 627, 628, 629 are detected, which occur sequentially. These peaks are detected in an effort to identify QRS complexes such as those of FIG. 4, with the apprehension that some of these peaks may be due to noise as seen in FIG. 5.

For purposes of detection, a number of criteria can be advantageously applied. For example, all peaks could have the same polarity, as QRS complexes do. Peaks of the opposite polarity can be ignored. In this example the polarity is positive, but it could equivalently be negative. Moreover, a peak can be deemed detected if it meets certain criteria, such as amplitude (e.g. relatively large rise over previous values, and relatively large fall back to about the same values), sharpness (e.g. relatively steep rise and relatively steep fall), and width (e.g. not wider beyond a threshold at mid-amplitude).

FIG. 6 also shows another time axis 648. Time axis 648 indicates only the time occurrences 641, 642, 643, 644, 645, 646, 647 of detected peaks 621, 622, 623, 624, 625, 626, 627 respectively.

In embodiments, pairs of the detected peaks can be established, where at least one of the pairs is established by peaks that do not occur sequentially. Such pairs may thus define time intervals. Then durations of the time intervals can be measured. In the example of FIG. 6, a pair of peaks 621 & 622 defines a time interval 651 between time occurrences 641 & 642. The same is true for time intervals 652 and 654, and so on.

It will be noted that a pair of peaks 621 & 623 define a time interval 653 between time occurrences 641 & 643. In this case, however, peaks 621 & 623 do not occur sequentially; rather, peak 622 occurs after peak 621 and before peak 623. And it will be recognized that, absent any noise and assuming perfect detection, time interval 653 will be a lot larger than either time interval 651 or 652. In fact, the duration of time interval 653 would be the sum of the durations of time intervals 651 and 652. Similarly, a pair of peaks 621 & 624, which do not occur sequentially, define a time interval 655 between time occurrences 641 & 644, and so on. More durations could be shown in FIG. 6.

In embodiments, these durations 651, 652, 653, 654, 655 can be used to compute heart rate 333 as further described later in this document.

In some embodiments, pairs are established among only some of the detected peaks. This can be implemented from the beginning, for example by not establishing all the possible pairs in FIG. 6. This can be implemented after some of the processing described later where all the possible pairs are established. At that time which a recognition value may be computed. Then a peak may be rejected, at least tentatively, for example according to a recognition criterion. It may turn out that rejecting the peak improves the recognition value, and detection of heart rate 333 becomes more robust.

In some embodiments, all possible pairs of the detected peaks are established. An example is now described.

Figure 7:
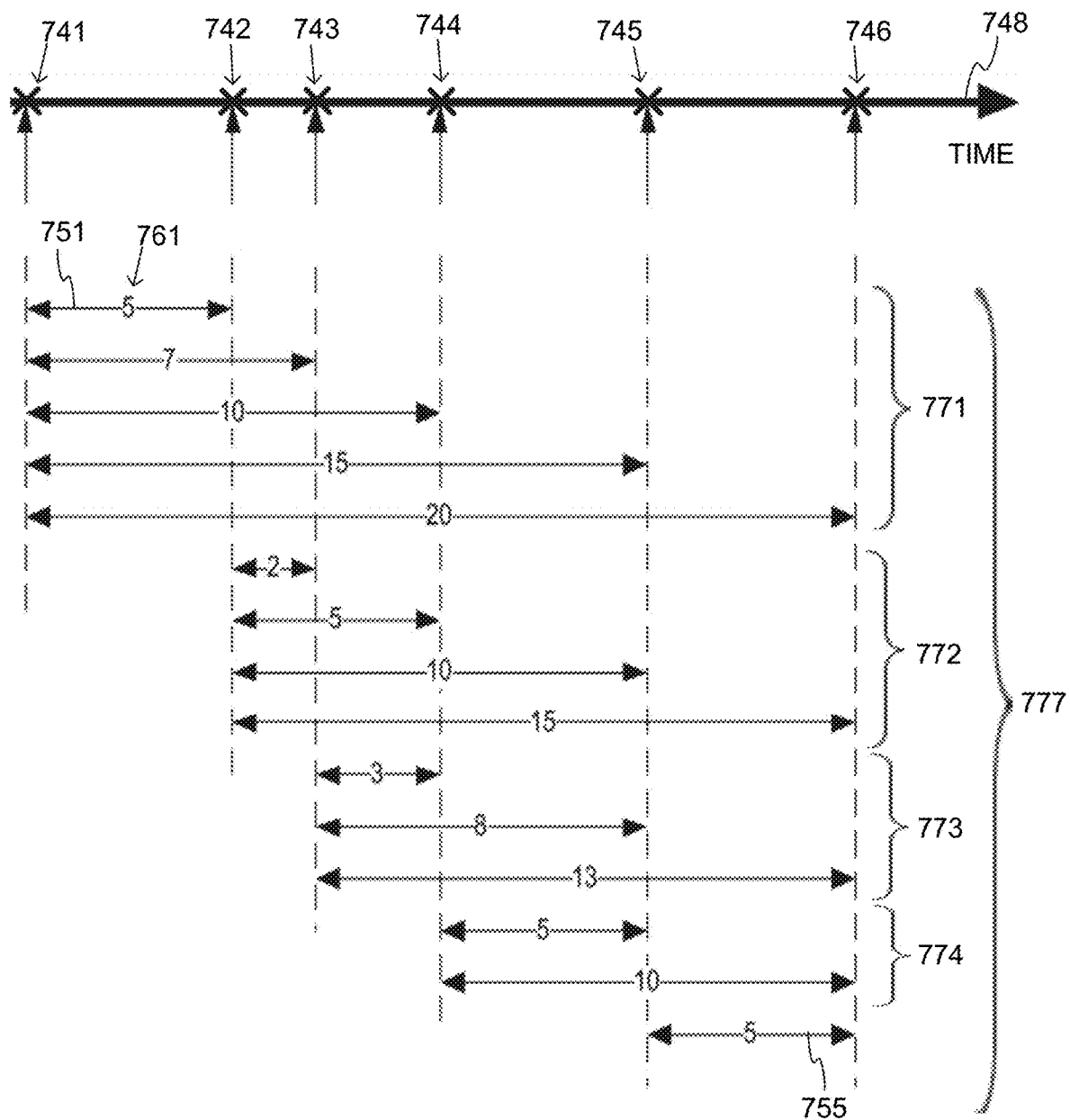
FIG. 7 is a time diagram for showing how a patient's heart rate may be detected from a noisy ECG signal, according to embodiments where all possible peak pairs are established.

FIG. 7 shows a time axis 748. Time axis 748 indicates only the time occurrences 741, 742, 743, 744, 745, 746 of peaks detected as described elsewhere in this document. For this discussion, pairs of peaks may be referred to by the time durations they define. For example, peaks at 741 & 742 define a time duration 751. In turn, time duration 751 has a duration indicated by arrow 761. In this example, time duration 751 has a measured duration of 5. Of course, this value of 5 can be in relative terms for this example.

It will be recognized that the peak at 741 defines a group 771 of time occurrences with each of the remaining considered peaks. Similarly, the peak at 742 defines a group 772 of time occurrences with each of the remaining considered peaks, and so on with groups 773, 774, and single time occurrence 755. As such, group 777 is a group of all possible pairs of peaks 741, 742, 743, 744, 745, 746. Each pair is shown by an arrow, with its measured duration as a number within the arrow.

In some embodiments, it can be identified which one of the measured durations occurs the most often. The heart rate of the patient can be computed from the identified duration. An example is now described.

Figure 8:
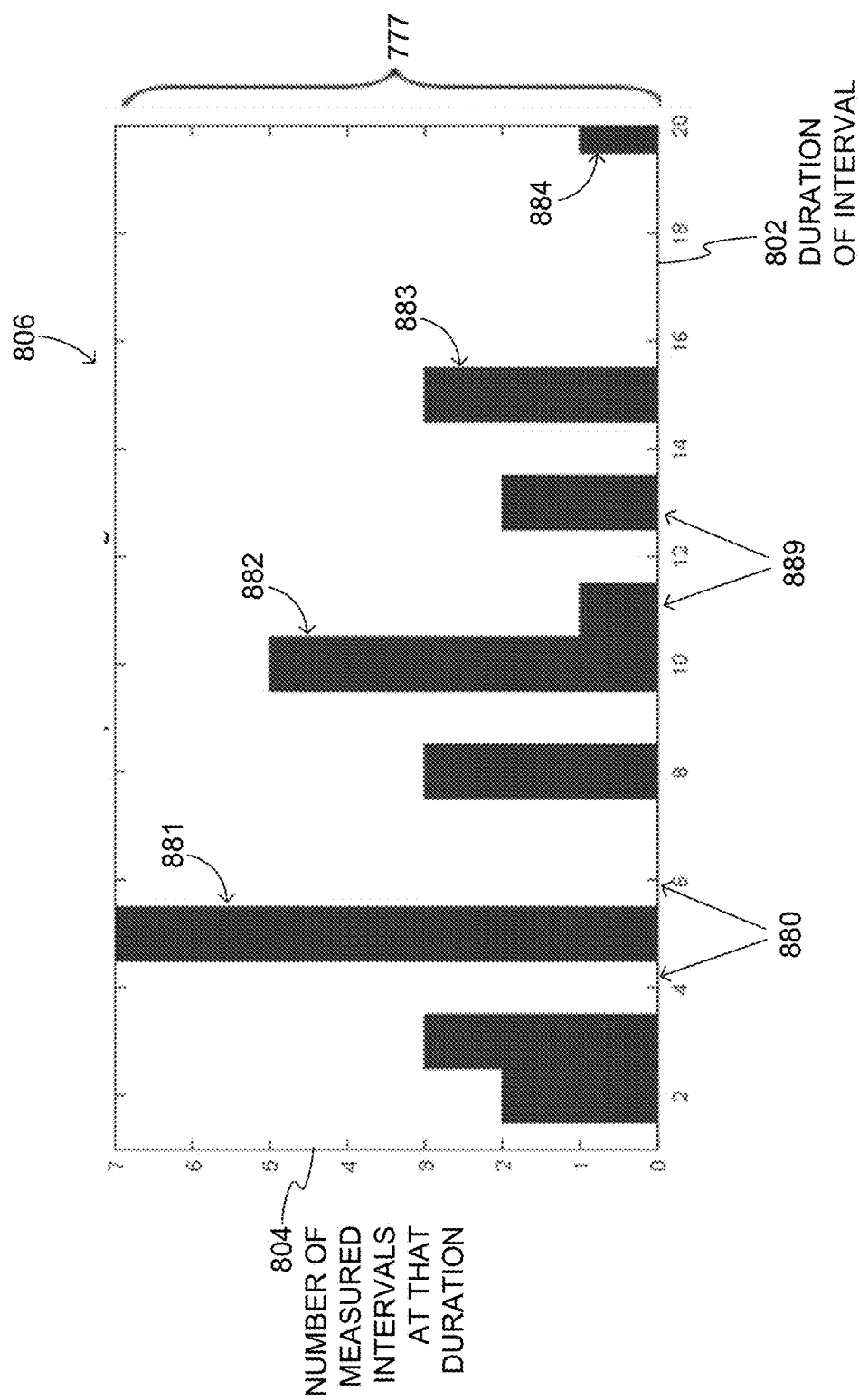
FIG. 8 is a bar chart for identifying which one of time durations measured in FIG. 7 best meets a plausibility criterion, according to embodiments.

FIG. 8 is a bar chart 806. Its horizontal axis 802 shows possible values for the measured durations of time intervals. Its vertical axis 804 shows numbers for how often a measured interval had the duration of horizontal axis 802. As such, bar chart 806 is not a time diagram.

Time durations 777 have been plotted in bar chart 806. As such, the time intervals defined by the peak pairs have been classified by their durations.

A salient feature of bar chart 806 is bar 881, which is the tallest. As such, it can be identified that the measured duration that occurs the most often has a duration of 5. Other features are bars 882, 883, 884, which occur at durations of 10, 15 and 20, and are the $2^{nd}$, $3^{rd}$, and $4^{th}$ harmonics of bar 881.

Bars 889 show some entries, which are presumed to be due to noise. In addition, some durations like 4 and 6, indicated by arrow 880, have no occurrences. This may be a result of the time durations having discrete enough values for this example or, equivalently, the bins of the bar chart time durations being wide enough.

As seen above, in some embodiments the ECG signal is sensed in samples, and the time durations are measured in numbers of samples. Again, if the bins of the bar chart are wide enough, they can produce a bar chart like bar chart 806, which is easy to work with even by having empty bins.

In some embodiments, from the measured durations, a representative duration can be identified that best meets a plausibility criterion. Such a plausibility criterion can be implemented in a number of ways. For example, as seen above, the plausibility criterion may include that the representative duration is the one that occurs the most often among the measured durations. Additional ways are described later in this document. In such embodiments, a heart rate of the patient can be computed from a duration indicated by the representative duration. Then it can be determined from the computed heart rate whether or not a shock criterion is met. Discharge circuit 255 can be controlled, responsive to the shock criterion being met, to discharge the stored electrical charge through patient 82 while support structure 170 is worn by patient 82, so as to deliver a shock to patient 82.

In embodiments, it is desired to add to these measurements durations of time intervals from additional channels. For example, in some embodiments the electrodes are further configured to sense an other ECG signal, and the processor is further configured to: detect other peaks occurring sequentially within the sensed other ECG signal, establish other pairs of the detected other peaks, at least one of the other pairs being established by other peaks not occurring sequentially within the sensed other ECG signal, and measure other durations of time intervals defined by the established other pairs. In such embodiments, the representative duration can be identified from both the measured durations and the measured other durations, thus providing more data points. Examples are now described.

Figure 9:
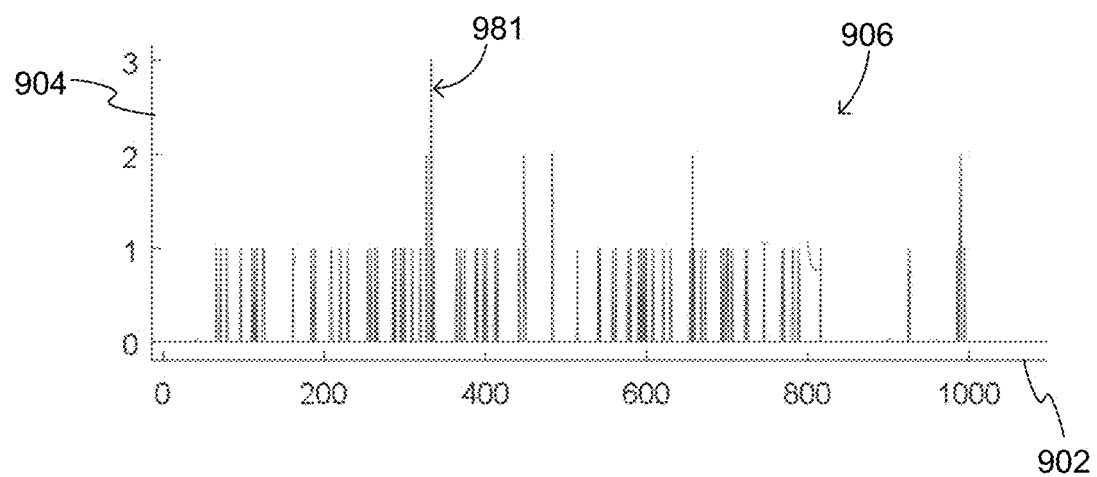
FIG. 9 is a bar chart of time durations measured in numbers of samples according to embodiments.

FIG. 9 is a bar chart 906. Its horizontal axis 902 shows possible values for the measured durations of time intervals. These values are in numbers of samples, for example as seen in axis 608 above. The vertical axis 904 of bar chart 906 shows numbers for how often a measured interval had the duration of horizontal axis 902. Intervals in this dataset range from 75-1000 samples, which could give a heart rate anywhere from 30-400 bpm (beats per minute). It will be observed that the most frequent occurrence is 3 for bar 981, which occurs at a value between 300 and 350, perhaps at 335 samples.

In some embodiments the heart rate can be computed from the representative duration. For example, if at FIG. 9 the representative duration is taken to be at 335 samples, the heart rate can be computed from that value, factoring in also the frequency with which the ECG signal is sampled.

In FIG. 9 it will be observed that the durations are measured in samples much more discretely than in FIG. 8, and so there are very few times when there is an occurrence of more than 1. To overcome this, in some embodiments processor 230 is further configured to discern clusters of the measured durations. In such embodiments, the representative duration is identified from the cluster that best meets a plausibility criterion. An example is now described.

Figure 10:
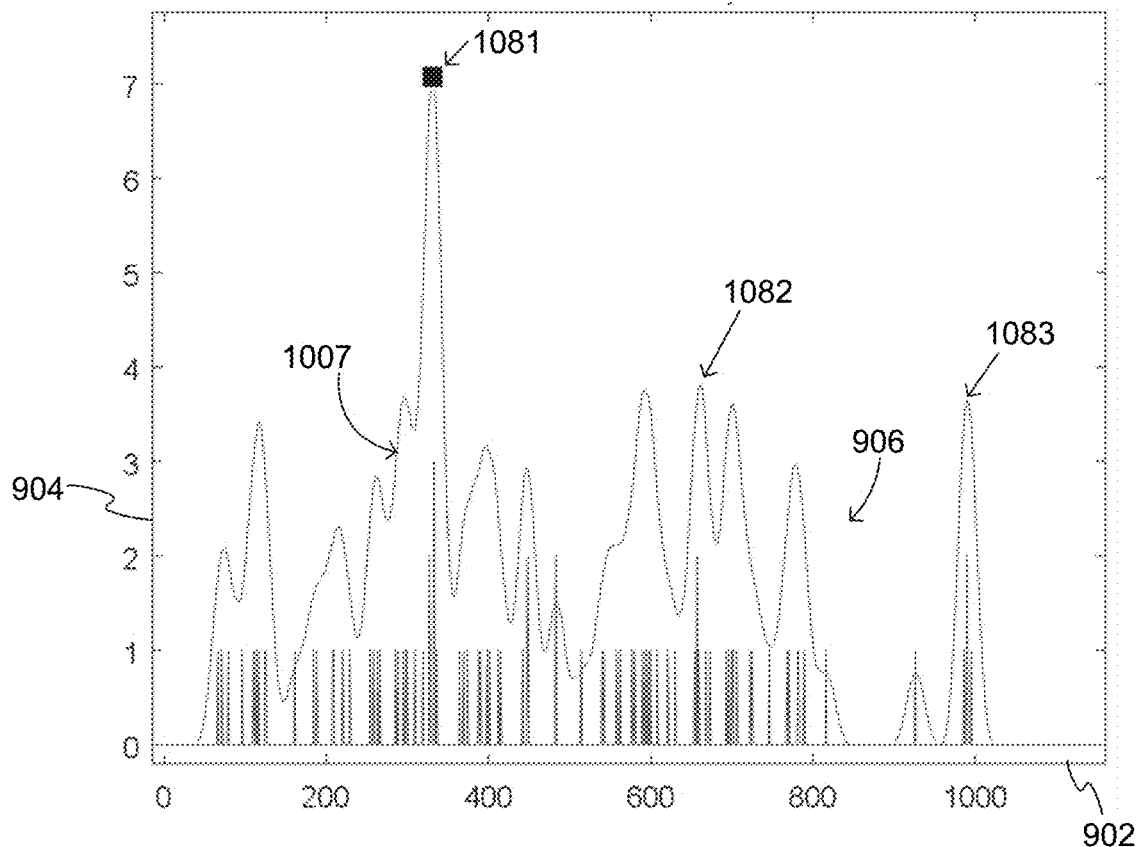
FIG. 10 is the bar chart of FIG. 9, where clusters of time durations have been further discerned, according to embodiments.

FIG. 10 repeats bar chart 906 of FIG. 9. In addition, FIG. 10 adds a computed line 1007 that identifies clusters of the bar charts, according to grouping of the values of the horizontal axis 902. Line 1007 shows a cluster with a maximum at point 1081, which corresponds to 331 samples. Line 1007 also shows clusters at a second harmonic 1082 (662 samples), and at a third harmonic 1083 (993 samples). As such, the cluster that best meets a plausibility criterion is at point 1081. Accordingly, the representative duration is identified at 331 samples, and as occurring about 7 times after the grouping. This representative duration corresponds to a heart rate of 90.6 bpm, which seems plausible.

While the chosen heart rate is 331 samples, it is possible that there was no duration measured with that exact value. It is further possible that the chosen heart rate does not correspond with the heart rate calculated for any given channel, which may raise questions. A WCD system incorporating this method may also have logic for deciding when to use the heart rate mode and when to use a simpler method. The mode tends to be beneficial when there is a substantial disagreement in the heart rate between channels and there is not an obvious reason for disqualifying one or more channels (like a dislodged ECG lead).

In some embodiments, the clusters are identified by filtering the measured durations. For example, in such embodiments, computed line 1007 can be generated by running a grouping kernel to identify the true R-R interval. Discreet time, digital implementations are preferred. The grouping kernel can be implemented as a boxcar Finite Impulse Response (FIR) filter with numerator coefficients of 1. This, effectively, counts up the intervals that are within the filter length. In addition, a standard FIR filter can be run, possibly in both directions, to smooth the result. This method is particularly attractive in a multichannel system because it is helpful to have numerically enough R-R intervals to work with. In a single channel system the mode may still stand out, but it may not stand out as much because there are fewer intervals altogether. Other methods of identifying clusters (or groups) may produce similar results.

In some embodiments, the plausibility criterion includes that a fraction of the identified representative duration occurs less often than an occurrence threshold. That fraction could be a half-, a third-, a quarter-harmonic and so on. For example, while the representative duration has a value of D and occurs M times, the plausibility criterion may include that a duration having a value of D/N occurs less often than M/N times, where N takes one of the values of 2, 3, 4 and 5. This helps mitigate against the possibility that an interval that is 2× the true interval may show up with the highest count, which can cause the heart rate to read half the actual value. If the patient's rhythm is non-shockable, then there is not much harm in this, but if the patient has a shockable rhythm, then such undercounting might cause a false no-shock decision. An example is now described.

Figure 11:
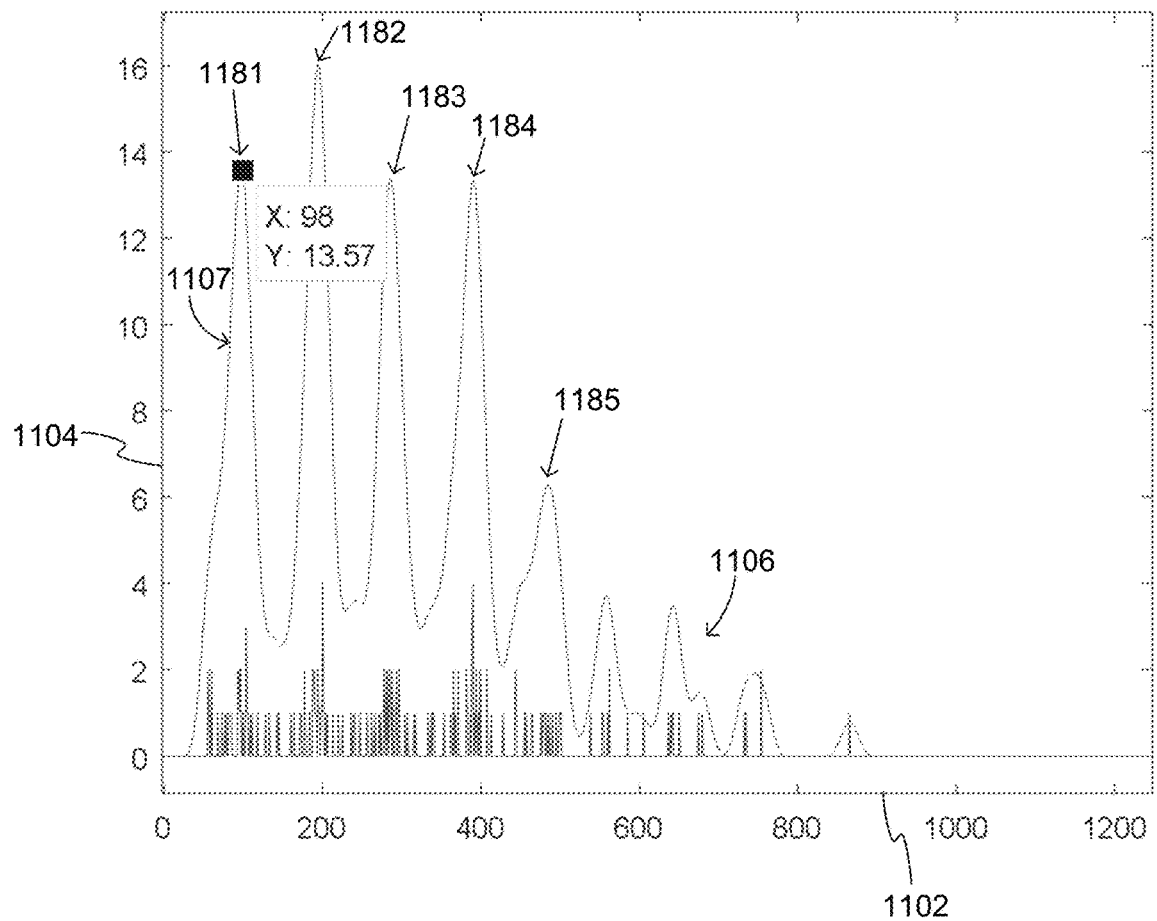
FIG. 11 is a bar chart of time durations where clusters have been discerned, and further where fractional harmonics have been accounted for, according to embodiments.

FIG. 11 is a bar chart 1106. Its horizontal axis 1102 shows possible values for the measured durations of time intervals, in numbers of samples. Its vertical axis 1104 shows numbers for how often a measured interval had the duration of horizontal axis 1102.

In addition, FIG. 11 adds a computed line 1107 that identifies clusters of the bar charts, according to grouping. Line 1107 shows a cluster with a maximum at point 1181, which corresponds to 98 samples, and occurs 13.57 times. Line 1107 also shows clusters at a second harmonic 1182, at a third harmonic 1183, at a fourth harmonic 1184, and at a fifth harmonic 1185.

It should be noted that the highest occurrence is at peak 1182. However, the half-harmonic of peak 1182 would be peak 1181, which does not occur less often than an occurrence threshold.

More particularly, in this example, the peak R-R interval would be at peak 1182, which occurs M=16 times, and is at 194 samples. The more advanced plausibility criterion included that a duration having a value of D/N, i.e. 194/2=97 samples occur less often than 16/2=8 times. Here, however, peak 1181 occurs 13.57 times at 98 samples, which is more than 8, and therefore peak 1182 is rejected as the representative duration. Accordingly, another representative duration is considered, which could be ½ or ⅓ the peak R-R interval. Here, peak 1181 is chosen, which passes the advanced plausibility criterion, even though it is shorter.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

FIG. 12 shows a flowchart 1200 for describing methods according to embodiments. According to an operation 1210, a first ECG signal of the patient may be sensed, such as ECG signal 317. Sensing can be by the electrodes.

According to another operation 1220, peaks occurring sequentially within the first ECG signal may be detected.

According to another operation 1230, pairs of the detected peaks may be established. At least one of the pairs may be established by peaks not occurring sequentially.

According to another operation 1240, durations of time intervals defined by the established pairs may be measured.

According to another operation 1250, a representative duration may be identified, which best meets a plausibility criterion. The representative duration may be identified from the measured durations.

According to another operation 1260, a heart rate of the patient may be computed. Computing may be from a duration indicated by the representative duration. According to another operation 1261, the computed heart rate of the patient may be stored in a memory. Computing may be from a duration indicated by the representative duration. According to another, optional operation 1262, the computed heart rate may be transmitted wirelessly, for example by a communication module. According to another, optional operation 1264, the computed heart rate may be displayed on a screen.

According to an operation 1268, a second ECG signal of the patient may be sensed, such as ECG signal 318. According to one more operation 1270, it may be determined whether or not a shock criterion is met. The determination may be from the second ECG signal of operation 1268. If at operation 1270 the answer is "no", indicated by a cross-out, then execution may return to a previous operation, such as operation 1210.

If at operation 1270 the answer is "yes", indicated by a checkmark, then according to another operation 1280, responsive to the shock criterion being met the discharge circuit may be controlled to discharge the stored electrical charge through the patient. Discharging may be while the support structure is worn by the ambulatory patient, so as to deliver a shock to the patient.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A wearable cardioverter defibrillator (WCD) system, comprising:
   a support structure configured to be worn by an ambulatory patient;
   an energy storage module configured to store an electrical charge;
   a discharge circuit coupled to the energy storage module;
   electrodes configured to sense a first Electrocardiogram (ECG) signal of the patient, and a second ECG signal after sensing the first ECG signal; and
   a processor configured to:
      detect peaks occurring sequentially within the first ECG signal,
      establish pairs of the detected peaks, at least one of the pairs being established by peaks not occurring sequentially,
      measure durations of time intervals defined by the established pairs,
      identify, from the measured durations, a representative duration that best meets a plausibility criterion,
      compute a heart rate of the patient from a duration indicated by the representative duration,
      determine from the second ECG signal whether or not a shock criterion is met, and control, responsive to the shock criterion being met, the discharge circuit to discharge the stored electrical charge through the patient while the support structure is worn by the patient so as to deliver a shock to the patient; and a memory configured to store the computed heart rate.

2. The WCD system of claim 1, further comprising:

a communication module configured to transmit wirelessly the stored heart rate.

3. The WCD system of claim 1, further comprising:

a screen configured to display the stored heart rate.

4. The WCD system of claim 1, in which all possible pairs of the detected peaks are established.

5. The WCD system of claim 1, in which the electrodes are further configured to sense another ECG signal of the patient distinct from the ECG signal and from the second ECG signal, and the processor is further configured to:

detect other peaks occurring sequentially within the other ECG signal, establish other pairs of the detected other peaks, at least one of the other pairs being established by other peaks not occurring sequentially within the other ECG signal, measure other durations of time intervals defined by the established other pairs, and the representative duration is identified from both the measured durations and the measured other durations.

6. The WCD system of claim 1, in which the plausibility criterion includes that the representative duration is the one that occurs the most often among the measured durations.

7. The WCD system of claim 1, in which the plausibility criterion includes that a fraction of the identified representative duration occurs less often than an occurrence threshold.

8. The WCD system of claim 1, in which the plausibility criterion includes that, while the representative duration has a value of D and occurs M times, and a duration having a value of D/N, where N takes one of the values of 2, 3, 4 and 5, occurs less often than M/N times.

9. The WCD system of claim 1, in which the heart rate is computed from the representative duration.

10. The WCD system of claim 1, in which the processor is further configured to:

discern clusters of the measured durations, and the representative duration is identified from the cluster that best meets the plausibility criterion.

11. The WCD system of claim 10, in which the clusters are identified by filtering the measured durations.

12. The WCD system of claim 10, in which the plausibility criterion includes that the representative duration is the one that occurs the most often among the measured durations.

13. The WCD system of claim 10, in which the plausibility criterion includes that a fraction of the identified representative duration occurs less often than an occurrence threshold.

14. The WCD system of claim 10, in which the plausibility criterion includes that, while the representative duration has a value of D and occurs M times, and a duration having a value of D/N, where N takes one of the values of 2, 3, 4 and 5, occurs less often than M/N times.

\* \* \* \* \*